United States Patent
Kunin et al.

(10) Patent No.: US 9,432,337 B2
(45) Date of Patent: Aug. 30, 2016

(54) SYSTEM AND METHOD FOR GENERATING AND MANAGING PRODUCT AUTHENTICATION CODES

(71) Applicant: Pharmasecure, Inc., Lebanon, NH (US)

(72) Inventors: Jay S. Kunin, San Diego, CA (US); Mihir Bellare, San Diego, CA (US); Nakul Pasricha, New Delhi (IN)

(73) Assignee: PharmaSecure, Inc., Lebanon, NH (US)

( * ) Notice: Subject to any disclaimer, the term of this patent is extended or adjusted under 35 U.S.C. 154(b) by 0 days.

(21) Appl. No.: 13/901,716

(22) Filed: May 24, 2013

(65) Prior Publication Data

US 2013/0332732 A1    Dec. 12, 2013

Related U.S. Application Data

(60) Provisional application No. 61/651,753, filed on May 25, 2012.

(51) Int. Cl.
*H04L 29/06* (2006.01)
*G06F 19/00* (2011.01)

(52) U.S. Cl.
CPC ....... *H04L 63/0428* (2013.01); *G06F 19/3456* (2013.01)

(58) Field of Classification Search
CPC ............... G06F 19/3456; G06F 21/64; H04L 63/0428; H04L 9/3236; H04L 9/3247
USPC ....................................................... 713/168
See application file for complete search history.

(56) References Cited

U.S. PATENT DOCUMENTS

| | | | | |
|---|---|---|---|---|
| 6,442,276 B1* | 8/2002 | Doljack | | 380/51 |
| 6,885,748 B1* | 4/2005 | Wang | | 380/201 |
| 7,257,545 B1* | 8/2007 | Hung | | 705/14.26 |
| 7,864,952 B2 | 1/2011 | Pauker et al. | | |
| 2002/0069185 A1* | 6/2002 | Kissner et al. | | 705/401 |
| 2005/0015674 A1* | 1/2005 | Haugh | | 714/38 |
| 2005/0273792 A1* | 12/2005 | Inohara et al. | | 719/330 |
| 2006/0015536 A1 | 1/2006 | Buchanan et al. | | |
| 2007/0205258 A1 | 9/2007 | Self et al. | | |
| 2008/0011841 A1* | 1/2008 | Self et al. | | 235/385 |
| 2008/0179390 A1 | 7/2008 | Harjani | | |
| 2009/0060180 A1* | 3/2009 | Schneider | | 380/46 |
| 2009/0119219 A1* | 5/2009 | Bleumer | | 705/62 |
| 2009/0310778 A1* | 12/2009 | Mueller et al. | | 380/44 |
| 2010/0318468 A1* | 12/2010 | Carr et al. | | 705/79 |

(Continued)

*Primary Examiner* — Don Zhao (74) *Attorney, Agent, or Firm* — Loginov & Associates, PLLC; William A. Loginov (57) ABSTRACT

A method for generating product authentication codes comprises allocating a lot identification value and a total lot size for an order of a plurality of product authentication codes, generating the plurality of product authentication codes based upon the lot identification value and the total lot size, and updating a counter table on an authentication server with the total lot size for the order of the authentication codes. A method for authenticating product codes comprises receiving a product code from a user of a product, decrypting the product code to obtain a sequence counter number unique to the product code and comparing the decrypted sequence counter number to a table of valid sequence counter number values to determine its authenticity. If the decrypted sequence counter number is authentic, it is added to an authentication table for future reference when operating to confirm a previous authentication of the sequence counter number.

17 Claims, 3 Drawing Sheets

(56) References Cited

U.S. PATENT DOCUMENTS

| | | | |
|---|---|---|---|
| 2012/0039469 A1* | 2/2012 | Mueller et al. | 380/252 |
| 2012/0066501 A1* | 3/2012 | Xiong | 713/171 |
| 2012/0111934 A1* | 5/2012 | Herzig | 235/375 |
| 2012/0224693 A1* | 9/2012 | Lei et al. | 380/270 |
| 2013/0124412 A1* | 5/2013 | Itwaru | 705/44 |
| 2013/0168450 A1* | 7/2013 | von Mueller et al. | 235/449 |

* cited by examiner

SYSTEM AND METHOD FOR GENERATING AND MANAGING PRODUCT AUTHENTICATION CODES

RELATED APPLICATIONS

This application claims the benefit of U.S. Provisional Application Ser. No. 61/651,753, filed May 25, 2012, entitled SYSTEM AND METHOD FOR GENERATING AND MANAGING PRODUCT AUTHENTICATION CODES, the entire disclosure of which is herein incorporated by reference.

FIELD OF THE INVENTION

This invention relates to systems and methods for managing product authentication codes for products, particularly pharmaceutical products.

BACKGROUND OF THE INVENTION

One major concern in the field of medicine is related to the distribution, sales and use of counterfeit drugs and other pharmaceutical products. In many countries around the world, medicines that are distributed and sold are fake, i.e. counterfeit. These counterfeit medicines are deliberately and fraudulently mislabeled with respect to identity and/or source. They can range from unknown random combinations of toxic substances to ineffective, inactive preparations, such as lacking an active ingredient. The results of counterfeit drugs are that either there is an ineffective treatment, a harmful outcome, or even worse, death, for a patient or other end user of the medicine.

In January 2010, the World Health Organization published an article on counterfeit drugs, describing the major health concern related with these illegal medicines. One counterfeit medicine for lowering blood sugar levels resulted in two deaths and nine hospitalizations in 2009 alone. In the United Republic of Tanzania in 2009, an antimalarial drug (Metakelfin) lacking sufficient level of the active ingredient was discovered in 40 pharmacies. This is particularly problematic in countries having weaknesses in their regulatory and enforcement systems. An estimated 1 in 4 packets of medicine sold in the street markets in developing countries is believed to be counterfeit. Over 50% of the medicines purchased over the Internet are from illegal sites that conceal their physical address, and have been found to be counterfeit.

More generally, in this environment (and even that of more-developed countries), a pharmaceutical manufacturer typically has little to no interaction or review of the sales of their medicines. After distributing their products to representatives or directly to end users, the pharmaceutical company does not communicate with the user thereafter. Likewise, the medical distributor simply sells products, with no feedback from users or sales information pertaining to the users. There is no interaction between the users of the medicines and the providers (manufacturers or distributors) or the products. There is not an effective way of eliminating these counterfeit medicines, accordingly there is a need for a system that verifies the validity of medicines, for the sake of all parties involved, particularly the end user of the medicine.

Moreover, distribution data in many emerging markets is often not accurate and/or is delayed. In general, drug distribution information is collected from pharmacy inventories and doctor prescriptions. In markets where pharmacies do not keep detailed real time electronic inventories or where patients regularly purchase drugs without a prescription, accurate distribution data is difficult, if not impossible, to gather. Any data that is gathered disadvantageously has a delay between the sale of medicines and the time the data is available to manufacturers and other parties involved in drug delivery.

Accordingly, there is a need for a system and method for generating and managing product authentication codes that are used in distribution of pharmaceutical drugs. Such a system should desirably provide a plurality of unique product authentication codes.

SUMMARY OF THE INVENTION

A method for generating product authentication codes comprises the steps of allocating a lot identification value and a total lot size for an order of a plurality of product authentication codes, generating the plurality of product authentication codes based upon the lot identification value and the total lot size, and updating a counter table accessible by an authentication server to include the total lot size for the order of the plurality of authentication codes. The counter table manages a lot identifier value for the codes and a begin and end value for the counter to generate code values and determine whether a particular code is authentic in accordance with the illustrative embodiments. The method is capable of providing and maintaining a plurality of unique product authentication codes without requiring an exhaustive list of every single unique product code that is (and/or has been) generated.

In accordance with a further illustrative embodiment, a method for authenticating product codes comprises receiving a product code from a user of a pharmaceutical product, decrypting the product code to obtain a sequence counter number unique to the product code and comparing the decrypted sequence counter number to a table of valid sequence counter number values to determine its authenticity. In the event that the decrypted sequence counter number is found to be authentic, it is added to an authentication table for future reference when operating to confirm a previous authentication of the sequence counter number.

BRIEF DESCRIPTION OF THE DRAWINGS

The invention description below refers to the accompanying drawings, of which.

DETAILED DESCRIPTION

A system and method for generating and managing product authentication codes, or "product codes", provides a plurality of product codes for products, particularly pharmaceutical products. Pharmaceutical companies are able to monitor the distribution of their medicines and products and users are also able to verify the validity of the medicine or product. The terms "medicine" and "product" as used herein are intended to cover either a medicine or a product, or both, or any other package of a pharmaceutical product that is "taken", consumed or otherwise used by a user and known in the art. The validity is determined through use of an identifying product code on the pharmaceutical product and securely managed.

Figure 1:
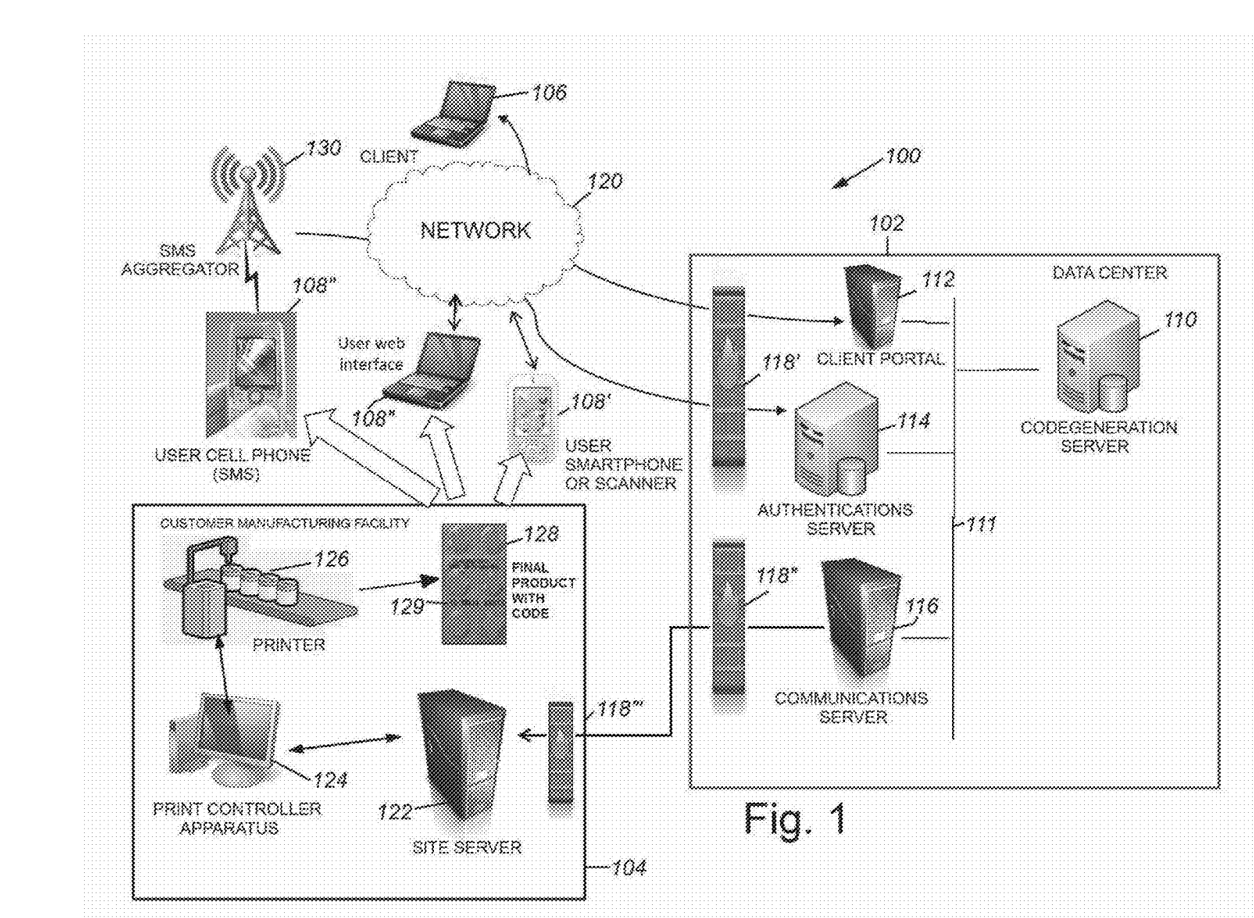
FIG. 1 is a block diagram of an overall system architecture for generating and authenticating product identification codes by employing a code generation server, according to an illustrative embodiment.

With reference to FIG. 1, there is illustrated a system 100 for practicing various exemplary and non-limiting embodiments. As illustrated, data center 102 provides bidirectional communication with client 106, user apparatus 108 and customer manufacturing facility 104. As described more fully below, data center 102 functions, generally, to receive requests from clients 106 for encrypted codes. In response, codes are generated at data center 102 and communicated, for example, to customer manufacturing facility 104 whereat the codes are received and affixed to one or more products including, but not limited to, pharmaceutical products. The generated codes are distributed to local sites, such as the manufacturing facility, which can have limited connectivity, while maintaining central management of the generated codes at the data center 102, or other appropriate location. Once delivered to users, each user can interface with data center 102 via user apparatus 108 to authenticate an encrypted code and receive a confirmation of authenticity. Note that, as used herein, the term "client" refers to the person(s) requesting generation of a plurality of codes, and "user" refers to the person(s) requesting authentication of at least one code.

In accordance with exemplary and non-limiting embodiments, data center 102 is comprised of code generation server 110, client portal 112, authentication server 114, communications server 116 and firewalls 118. It is understood that, while described with reference to separate and distinct entities, the functionality of various permutations of client portal 112 and servers 110, 114, 116 can be combined into a single computing device or spread out amongst various other (distinct) computing devices as desired. As described more fully below, communications originating either from client 106 or user apparatus 108 are received at data center 102 at firewall 118'. In the event that client 106 is communicating with data center 102 to, for example, request the generation of codes, client communications are communicated from firewall 118' to client portal 112. Client portal 112 can communicate via network 111 with code generation server 110 to facilitate the generation of requested codes. Network 111 can be any form of wired or wireless network capable of transmitting data between and amongst client portal 112 and servers 110, 112, 114, 116.

The code generation server 110, as described in greater detail below with reference to FIG. 2 and counter table 222, can generate multiple groups of codes in parallel on independent servers. More particularly, the code generation server is capable of generating a group of codes without requiring communication between the individual servers that are generating the individual codes. Because the codes are generated as a group (or a "lot") based upon the total number of codes that are requested, a lot of codes are supplied to each server so that the servers can independently generate the individual encrypted codes without communicating with each other, and without knowing which codes are generated at each server. Accordingly, the code generation system and method is easily scalable depending upon scale and size (i.e., number of codes) needed for a particular application. Also, the code generation system and methods are distributed, but centrally controlled, so that the codes can be generated at the point of use (for example, at the manufacturing facility).

Communications originating at user apparatus 108 can be communicated, such as via network 120, to firewall 118' and onward to authentication server 114. As described more fully below, in this manner, bidirectional communication between authentication server 114 and user apparatus 108 can be utilized to receive requests for code authentications from a user as well as user information, containing particular information about the user, and to return authenticating information to the user.

In accordance with the illustrative embodiment, one code generation server 110 can support multiple (unlimited) authentication servers 114. The authentication servers can be virtual (i.e., software-based) or each as a dedicated physical computing device, and are each constructed and arranged to each answer a different address (channel) such that requests for authentication are appropriately routed depending upon the particular channel utilized in requesting authentication. In an illustrative embodiment, the channel can be medium-specific (i.e., the authentication servers vary based upon the particular medium used for authentication), geographic-specific (i.e., the authentication servers vary based upon the geographical location), or specific to another preselected parameter relevant to authentication of products. For example, for medium-specific authentication servers (or authentication "sites"), authorization requests sent to a phone number for Short Message Service (SMS) messages are sent to one authentication server and authorization requests sent to a Uniform Resource Locator (URL) for web-based requests can go to a second authentication server, with each channel used for sending the authentication requesting having a respective authentication server for processing and authentication of an encrypted product code. This allows for multiple products to be managed in a same geographical region (for example, food and drugs can both be monitored in India). Likewise, this allows for a single product code to be managed in multiple geographical locations (for example, a pharmaceutical product can be coded for India, Nigeria, the United States, and other countries) and the product is only able to be authenticated when in the geographical location for which it was intended. In an illustrative embodiment, geographic-specific servers allows for geographical separation (in terms of authentication) of the product codes, such that product codes generated in one geographical location are sent to one authentication server, and product codes generated in another geographical location are sent to another authentication server. More particularly, pharmaceutical products in India can be authenticated using one authentication server while pharmaceutical products in Nigeria can be authenticated using another authentication server. According to this example, products in India can be authenticated by sending an SMS to a particular phone number, by visiting a web page or by using a mobile application after registering a geographical location, which are all handled by an authentication server. Likewise, products in Nigeria can all be authenticated by another authentication server, whether via SMS message, web-based URL request, or a mobile application. The geographic-specific product codes for Nigeria, for example, are constructed and arranged such that, if sent through the India input channels, would return either an "invalid" (i.e. not a valid code) response, or an incorrect response (if the same code happens to be associated in India for a different product). If, however, Nigeria codes come in through any appropriate channel for Nigeria authentication, the requests are correctly authenticated. In accordance with this example, all channels of authentication (i.e., SMS gateway, separate product-specific webpage or separate mobile app) authenticate codes in the same manner, with an authentication server being provided for each geographic location to provide geographic-specific authentication of products.

Network 120 comprises any appropriate communication network known in the art, including a local area network (LAN), wide area network (WAN), the broad worldwide Internet, cellular telephone messaging and communication, including Short Message Service (SMS) messages, through a cellular tower network, or any other appropriate network or secured connection, such as HTTPS (Hypertext Transfer Protocol Secure) or SFTP (Secure File Transfer Protocol). The product codes 129 uploaded to the system 100, as well as the response "verification" messages transmitted to the user can be in any appropriate form of communication through any network known in the art. For example, the messages can be standard message (SMS, MMS (multimedia messaging service) or other, smartphone application communication, USSD (Unstructured Supplementary Service Data)) having a particular series of characters and letters used to authenticate a product (such as #AUTHENTICATE*CODE DATA), using a Twitter handle to tweet the authentication code to the appropriate entity, or through the Internet in general via an electronic internet-based message.

Communication server 116 can communicate information, such as generated codes received from code generation server 110 via network 111, to customer manufacturing facility 104. Once received at firewall 118''', data is communicated to site server 122. Codes communicated to site server 122 can be accessed by print controller apparatus 124 and utilized to direct printer 126 to print or otherwise affix product codes 129 onto products 128. As illustrated, products 128 are then distributed, such as through commerce, to users. While illustrated as user apparatus 108'-108''', it is understood that each user apparatus is operated by a user, specifically, a user of product 128. "User" as defined herein represent consumers, end-users, including purchasers, of the products as well as representatives of the pharmaceutical company that assist in the distribution and sales of the medicines to end users, including, but not limited to, entities in the distribution chain, such as pharmacists or other retailers, wholesalers, and distributors. As a result, both user apparatus 108 and "user" can be recited in an interchangeable manner when referring to an entity requesting authentication of a product code 129.

Once distributed, products 128 can be authenticated by users via user apparatus 108. Examples of user apparatus include, but are not limited to, smart phone or other appropriate scanner user apparatus 108', web interface user apparatus 108'' and cell phone user apparatus 108'''. As illustrated, smart phone or scanner user apparatus 108' and web interface user apparatus 108'' can engage in bidirectional communication with data center 102 via a wired or wireless network, such as network 120. Similarly, cell phone user apparatus 108''' can make use of SMS aggregator 130 to implement bidirectional communication with data center 102. While illustrated with reference to various forms of user apparatus 108, it is understood that user apparatus 108 encompasses any and all platforms capable of gathering, such as via a user interface, information from a user, transmitting the information to data center 102 and receiving a response, such as a product authentication, from data center 102.

Figure 2:
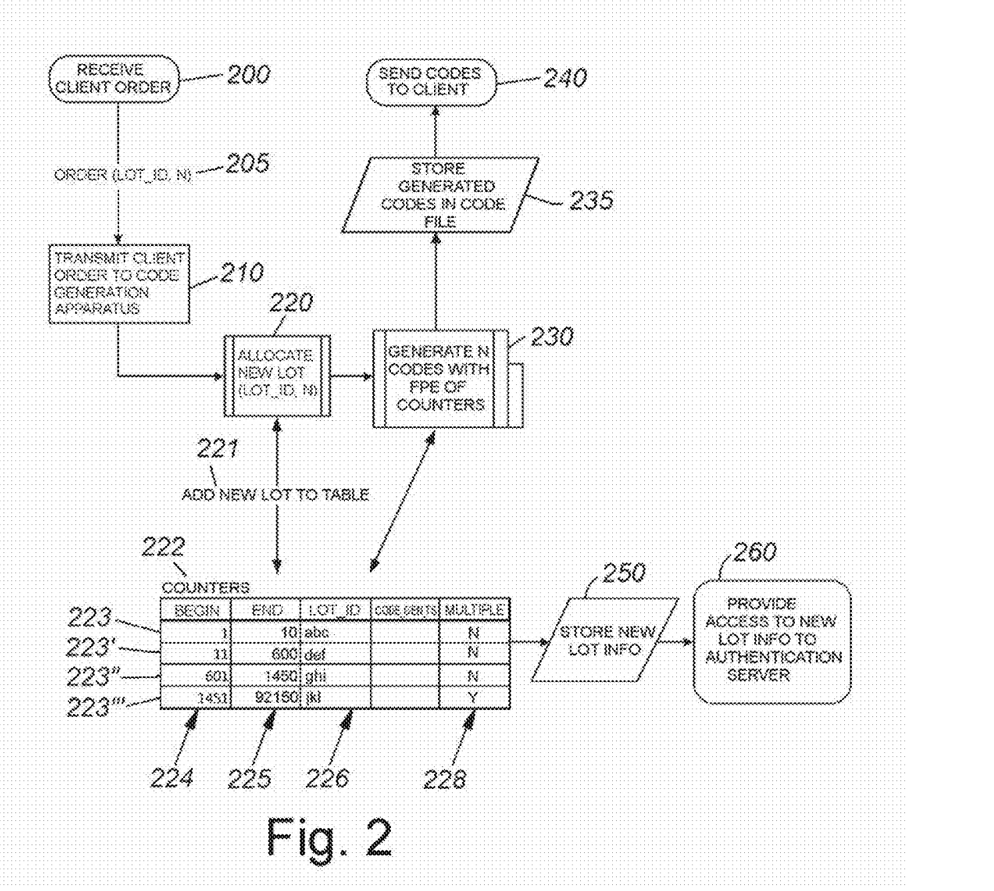
FIG. 2 is a flow chart diagram of a procedure for ordering, allocating and generating codes using the code generation server and a counter table, according to the illustrative embodiment.

With reference to FIG. 2, there is illustrated a flow chart of an exemplary and non-limiting embodiment of the process of code generation. The process begins at step 200 whereat a client order is received, such as by code generation server 110. As described above, the client order can be entered and communicated to code generation server 110 by client portal 112 utilizing, for example a computing device comprising a user interface. This can be a consumer entering a product code for authentication using their cell phone, smart phone, tablet, laptop, personal computer, or other electronic device. In addition to receiving a client order, client portal 112 can further engage in bidirectional communication with client 106 and host, for example, a web site. Such a web site can function to validate the identity of client 106, facilitate client access to previous client requests and the like. As illustrated, the client order 205 comprises, at least, a lot identifier, ("lot_id"), and a number of requested codes, (N). For example, a client order comprising (abc,10) specifies a lot having lot identifier "abc" and consisting of 10 codes.

At step 210, the received client order is transmitted to a code generation apparatus. In an exemplary embodiment, the code generation apparatus comprises code generation server 110 described above. Next, at step 220, code generation server 110 allocates a new lot corresponding to the requested lot identifier and number of requested codes N. In the present example, a lot having lot identifier "abc" is allocated having a beginning sequence counter number 1 and an ending sequence counter number 10. As illustrated, the new lot is added to the table 221 and this lot allocation data is stored in counter table 222 comprising, for example a plurality of records 223. While each record includes, at least, the beginning sequence counter number 224 and ending sequence counter number 225 and the associated lot identifier 226, each record can include various other attributes such as timestamps and data related, for example to the preferences of a client such as, for example, a flag 228 indicating whether or not multiple authentications of a generated code are permitted. Note that each record 223 records the first and last sequence counter number forming a range of N elements within which all of the allocated sequence counter numbers fall. In this manner, any number or range of sequence counter numbers can be represented with two numbers thus saving storage space. Counter table 222 is stored so as to be accessible by code generation server 110. The counter table 222 can be stored locally and/or at a remote location, automatically updated or otherwise stored in accordance with standard data storage techniques known to those skilled in the art.

Next, at step 230, N codes, corresponding to the added record of counter table 222, are generated by applying encryption to the counter sequence numbers. In an exemplary embodiment, format-preserving encryption (FPE) is utilized. FPE refers to encrypting in such a way that the output is in the same format as the input. FPE enables the generation of pseudorandom unique tokens in a fixed format. For example, suppose product codes (for example 129 in FIG. 1) need to be "randomly" generated, but must be unique and exactly 10 digits long. To create a plurality of pseudo-random product codes ten digits long, a FPE cipher on the domain {0000000000, . . . , 9999999999} is applied to the range of sequence counter numbers (0, 1, 2, . . . ) with the resulting encrypted values becoming the product codes 129. Commonly requiring the application of a key known to the encoding and decoding entity, i.e., data center 102, each product code 129 can be decrypted to yield the sequence counter number and domain value from which it was derived. In this manner data center 102, and particularly authentication server 114, can operate to retrieve a sequence counter number form an encrypted product code 129 as explained more fully below.

Next, at step 235, the generated codes are stored in a codes file. The codes file can be any formatted data file capable of storing the generated codes for retrieval such as by, for example, customer manufacturing facility 104. At step 240, the codes are sent to customer manufacturing facility 104 for processing and to be affixed to product 128. In accordance with an exemplary and non-limiting embodiment, the codes file is communicated from communication server 116 to firewall 118''' and then to firewall 118'''' of customer manufacturing facility 104. In accordance with an exemplary embodiment, instances of the codes including, but not limited to, the codes file, can be encrypted via any means known in the art to ensure the secure communication of codes to manufacturing facility 104.

The new lot data having been allocated in counter table 222 at step 220, counter table 222 is stored at step 250 and, at step 260, access to counter table 222 is provided to authentication server 114. The electronic storage of the counter table and access of the data contained therein is highly variable within ordinary skill in accordance with standard data storage and access techniques, depending upon the particular application for the codes.

Figure 3:
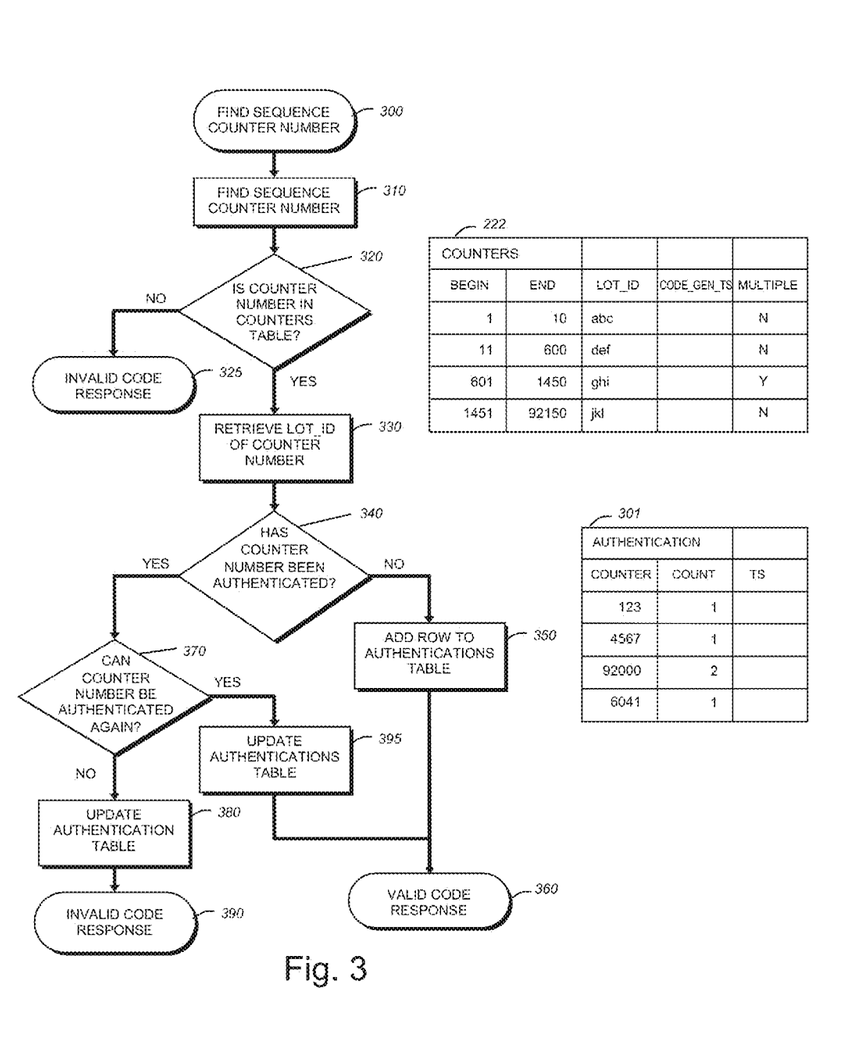
FIG. 3 is a flow chart diagram of a procedure for authenticating codes generated using a counter table, according to the illustrative embodiment.

With reference to FIG. 3, there is illustrated a flow chart of an exemplary and non-limiting embodiment of the process of code authentication. In addition to the flow chart, reference is made to exemplary counter table 222 (replicated from FIG. 2) and authentication table 301 the operation of which is discussed more fully below. At step 300, product code 129 is received. In accordance with an exemplary embodiment, a user of product 128, such as a pharmaceutical product, communicates with data center 102 to authenticate the product code 129. For example, a user utilizing cell phone user apparatus 108''' can dial a number, send a message, or otherwise establish a connection to communicate with authentication server 114 and proceed to enter product code 129, using a user interface comprising a part of cell phone user apparatus 108'''.

The authentication request can appropriately be transmitted to a channel-specific authentication server that is constructed and arranged to receive a particular type of authentication request. More particularly, the authentication server 114 can comprise a plurality of individual (real or virtual) authentication servers, each dedicated to a particular channel used for authentication of encrypted product codes. For example, one authentication server can be employed for SMS messages sent to a phone number, and another authentication server can be implemented for web-based requests sent to a URL. Moreover, in a geographic-based channel authentication system, one authentication server can be employed for a first geographic location, and a second authentication server can be employed for a second geographic location. In accordance with further embodiments, the codes can be routed depending upon the specific code data associated with the product. In this manner, channel-specific (medium-specific, geographic-specific or code-specific) authentication servers can be implemented to automate and improve the generation and authentication of codes in accordance with the illustrative embodiments herein.

Next, at step 310, product code 129 is decoded, or decrypted, to obtain the sequence counter number encrypted therein. In accordance with an exemplary embodiment, a key is applied with FPE to decrypt product code 129 into the sequence counter number utilized to encrypt product code 129. At step 320, a check is performed to confirm whether or not the decrypted sequence counter number appears in counter table 222. For example, consider the instance where the decrypted sequence counter number is "109876". As illustrated in exemplary counter table 222, sequence counter number "109876" does not fall between any of the exemplary begin and end values of any of the records in counter table 222. As a result, product code 129 is determined to be invalid at step 325. Upon determining product code 129 to be invalid, authentication server 114 communicates information indicative of an invalid product code 129 to user apparatus 108 from which the query originated. Conversely, consider the instance where the decrypted sequence counter number is "2003". As illustrated in exemplary counter table 222, sequence counter number "2003" falls between the begin and end values of the record associated with lot identifier "jkl" in counter table 222.

As a result, processing continues to step 330 whereat the lot identifier associated with the decrypted sequence counter number is retrieved. At step 340, a determination is made if the decrypted sequence counter number has been previously authenticated. Authentication table 301 contains a record for every product code 129 that has been previously authenticated. Specifically, each record records the sequence counter number decrypted from received product code 129 and a "count" value indicating the number of times the particular sequence counter number has been authenticated. As a result, if a decrypted sequence counter number does not appear in authentication table 301, processing continues to step 350 whereat a row is added to authentication table 301 signifying the first authentication of the decrypted sequence counter number. Processing then continues to step 360 whereat a valid response indicating an authenticated product code 129 is communicated to, for example, client 106 or user apparatus 108 from whence the request for authentication originated. Therefore, a counter table can be saved, requiring only minimal storage usage, and the only individual codes that are stored are the codes that have been authenticated. This significantly reduces the space needed for data storage, while allowing a very large amount of codes to be generated.

It is possible, though unlikely, that a counterfeit product code 129 can appear as authenticated using the process described above. Specifically, if a product code 129 was copied from an authentic product 128 and reprinted in nefarious fashion on a counterfeit item, efforts to authenticate the misappropriated product code would succeed. However, misappropriating product codes 129 in this manner is time consuming and rather impractical as typical lots of products can range in the thousands, tens of thousands or even hundreds of thousands. In yet another scenario, it is possible, though highly unlikely, that a randomly generated counterfeit product code 129 would map to a valid range of sequence counter numbers associated with a valid lot identifier as described above. With these two scenarios in mind, the communication of the valid response at step 360 can be augmented to provide additional information capable of further authenticating product 128 for which authentication was requested.

For example, authentication server 114 can access one or more databases, such as relational databases, to retrieve additional information associated with, for example, the lot identifer of the authenticated product code 129. Such information can include, but is not limited to, product type, batch number, etc. This additional data can be transmitted to client 106 or user apparatus 108 along with the authentication. For example, authentication server 114 can communicate with cell phone user apparatus 108 with a message reciting "Product code 4567 having batch number 347 and affixed to 50 count bottle of 20 mg aspirin tablets is authenticated." Because batch numbers are printed near product code 129 and the type of product is easily discernible, the communication of such additional information provides further protection against product code 129 misappropriation and random product code 129 generation. A user can verify the authenticity by confirming the correct product code is assigned to each product.

Returning to step 340, if it is determined that there is already a row in authentication table 301 for the decrypted sequence counter number, indicating a previously authenticated sequence counter number, processing continues to step 370 whereat a check is performed to determine if the sequence counter number can be authenticated again. In an exemplary embodiment, a query can be made using the lot identifier from step 330 to check the status of a "multiple" flag indicating whether or not multiple authentications are permitted. If further authentication is not permitted, processing continues to step 380 where the authentication table 301 is updated, such as by updating a column (not shown) indicative of a number of previous attempts to authenticate the sequence counter number and, at step 390, an invalid response is communicated to, for example, user apparatus 108.

Conversely, if, at step 370, it is determined that the sequence counter number can be authenticated an additional time, processing proceeds to step 395 whereat authentication table 301 is updated to reflect the new authentication and processing continues to step 360 whereat a valid response indicating an authenticated product code 129 is communicated to, for example, client 106 or user apparatus 108 from whence the request for authentication originated.

The code generation and authentication procedure outlined above allows for rapid generation of codes, including parallel processing, by knowing simply the counter start value, number of codes N and the lot identifier number, and simultaneously allows users to verify product codes without requiring system 100 to maintain an exhaustive list of every code that has been generated, but instead a counter table 222 with the ranges of codes that have been generated.

The systems and methods herein allow for parallel generation of codes to be used for a variety of different applications. For example, the product codes can be printed directly on the packages of pharmaceutical products for retail sale, or for wholesale sale, through distributors, containing multiple uniquely-coded retail packages. The product codes can also be printed on containers containing the packages of the wholesale packages, to track and/or monitor status and distribution of the packages. The product codes can be applied at various stages during manufacturing of a product to monitor the manufacturing thereof. The product codes can also be printed on labels which are affixed to products or containers. The encrypted product codes can be printed on packages of fast-moving consumer goods (FMCG), otherwise known as consumer packaged goods, for example Halal or kosher foods, cigarettes, and similar packaged goods. The encrypted product codes can also be inscribed or embossed on high-value products, such as automotive parts, aerospace parts, and other similar parts readily apparent to those skilled in the art.

In addition, data collected at data center 102 indicative of authentication requests including, but not limited to, user and client id, time of authentication, product type, user and client location and the like can be stored to provide a database of pharmaceutical consumption metrics and characteristics. Such data can be mined so as to, for example, detect the progression or onset of disease and epidemics. Such data can further be packaged and sold to third parties for marketing or research purposes.

The foregoing has been a detailed description of illustrative embodiments of the invention. Various modifications and additions can be made without departing from the spirit and scope of this invention. Features of each of the various embodiments described above can be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, the procedures have been described with reference to managing medicines or particular drugs or other products provided by a pharmaceutical company. However, the teachings herein are broadly and readily applicable to any medicine, and indeed to any consumer product, that is sold or distributed, for which data is available. Additionally, the systems and applications herein are described as residing on a particular computing environment, database structure or client-server architecture. However, the type and arrangement or systems and components is highly variable within ordinary skill to achieve the functions described herein. In addition, any of the procedures, functions and/or processes described herein can be performed using electronic/computer hardware, software consisting of a non-transitory computer-readable medium of program instructions, or a combination of hardware and software. Accordingly, this description is meant to be taken only by way of example, and not to otherwise limit the scope of this invention.

What is claimed is:

1. A system for generating and authenticating product codes, the system comprising:

a client computing device that receives a request from a user for a predetermined quantity of unique, pseudo-random codes to be applied to one or more products or packaging and transmits the request to at least one code generation computing device of a plurality of code generation computing devices, wherein each unique, pseudo-random code of a first predetermined quantity of unique, pseudo-random codes associated with a first request is unique from each unique, pseudo-random code of a second predetermined quantity of unique, pseudo-random codes;

the at least one code generation computing device that receives the request from the client computing device and generates a predetermined quantity of sequential codes in response to the request for the predetermined quantity of unique, pseudo-random codes are wherein the predetermined quantity of unique, pseudo-random codes are generated in a specific format from the predetermined quantity of sequential codes using a format-preserving encryption (FPE) process and a single data element generated to specify that the predetermined quantity of unique, pseudo-random codes associated with the predetermined quantity of sequential codes that have been issued, the single data element being a highest numbered sequential code that has been generated using the FPE process; and an authentication computing device that receives authentication requests from the user for authentication of at least one unique, pseudo-random code of the predetermined quantity of unique, pseudo-random codes, and thereafter determines authenticity of the one or more products or packaging associated with the at least one unique, pseudo-random code that the user has requested to be authenticated by decrypting the at least one unique, pseudo- random code that the user has requested to be authenticated using the FPE process to generate at least one decrypted sequential code and comparing the decrypted sequential code to the single data element, the authenticity being determined when the decrypted sequential code is equal to or less than the single data element.

2. The system as set forth in claim 1 further comprising a communication device that transmits the predetermined quantity of unique, pseudo-random codes to a manufacturing facility.

3. The system as set forth in claim 1 wherein the predetermined quantity of unique, pseudo-random codes are generated in parallel for each of a plurality of variety of applications.

4. The system as set forth in claim 1 wherein the predetermined quantity of unique, pseudo-random codes are applied to a pharmaceutical product for retail or wholesale sales.

5. The system as set forth in claim 1 wherein the predetermined quantity of unique, pseudo-random codes are printed on a label to be affixed to a product such that the product codes need not be printed directly on the product.

6. The system as set forth in claim 1 wherein the predetermined quantity of unique, pseudo- random codes are printed directly on packages of fast-moving consumer goods.

7. The system as set forth in claim 1 wherein the predetermined quantity of unique, pseudo-random codes are inscribed or embossed on high-value products.

8. The system as set forth in claim 1 wherein the client computing device, the at least one code generation computing device and the authentication computing device are combined within a single computing device or spread out over a plurality of distinct computing devices.

9. The system as set forth in claim 1 wherein the requests for generation and authentication of the predetermined quantity of unique, pseudo-random codes are transmitted and received over a wired or wireless network.

10. The system as set forth in claim 9 wherein the wired or wireless network comprises one or more of a local area network (LAN), a wide area network (WAN), the Internet, a cellular tower network, a short-message-service (SMS) message, a Hypertext Transfer Protocol Secure (HTTPS) or a Secure File Transfer Protocol (SFTP).

11. The system as set forth in claim 1 wherein the at least one code generation computing device is in communication with a second authentication device, and wherein each of the authentication computing device and the second authentication device is constructed and arranged to receive the authentication requests respectively from a particular channel.

12. The system as set forth in claim 11 wherein the particular channel comprises one or more of a Short Message Service (SMS) message request sent to a phone number or a web-based request via a Uniform Resource Locator (URL).

13. The system as set forth in claim 11 wherein the particular channel comprises a geographic-based location.

14. The system as set forth in claim 1 wherein the at least one code generation computing device comprises a plurality of independent servers that allow for code generation at a point of use on the one or more products or packaging.

15. A method for generating and authenticating product codes, the method comprising steps of:

receiving a request from a user via a client computing device for a predetermined quantity of unique, pseudo-random codes to be applied to one or more products or packaging, wherein each unique, pseudo-random code of a first predetermined quantity of unique, pseudo-random codes associated with a first request is unique from each unique, pseudo-random code of a second predetermined quantity of unique, pseudo-random codes;

transmitting the request to at least one code generation device of a plurality of code generation devices;

generating a predetermined quantity of sequential codes in response to the request for the predetermined quantity of unique, pseudo-random codes;

generating the predetermined quantity of unique, pseudo-random codes in a specific format from the predetermined quantity of sequential codes using a format-preserving encryption (FPE) process running on the at least one code generation device;

generating a single data element to specify that the predetermined quantity of unique, pseudo-random codes associated with the predetermined quantity of sequential codes have been issued, the single data element being the highest numbered sequential code that has been generated using the FPE process; and determining authenticity of at least one code that a user has requested to be authenticated of the predetermined quantity of unique, pseudo-random codes by an authentication computing device by decrypting the at least one unique, pseudo-random code that the user has requested to be authenticated using the FPE process to generate at least one decrypted sequential code and comparing the decrypted sequential code to the single data element in response to an authentication request, the authenticity being determined when the decrypted sequential code is equal to or less than the single data element.

16. The method as set forth in claim 15 wherein the step of generating the predetermined quantity of sequential codes further comprises steps of:

allocating a lot identification value and a total lot size for an order of a plurality of product authentication codes;

generating the plurality of product authentication codes based upon the lot identification value and the total lot size; and updating a counter table on the authentication computing device to include the total lot size for the order of the plurality of the product authentication codes.

17. The method as set forth in claim 15 wherein the step of the determining authenticity comprises:

identifying a channel associated with the authentication request; and assigning the authentication request to a channel-specific authentication server for authenticating the at least one code that the user has requested to be authenticated.

* * * * *